Figure 1:
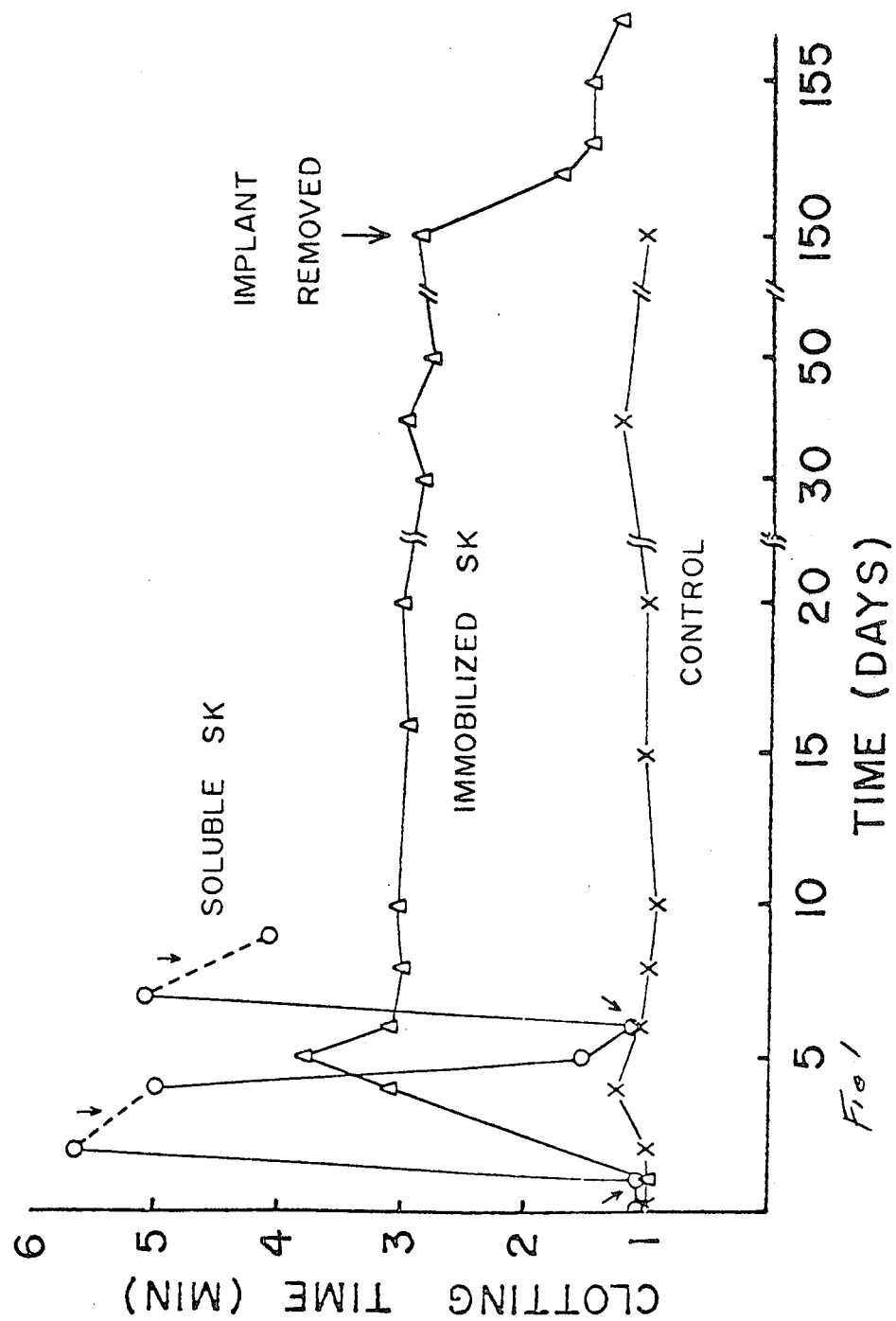

United States Patent [19]

Everse et al.

[11] 4,305,926

[45] Dec. 15, 1981

[54] IMMOBILIZATION OF STREPTOKINASE

[76] Inventors: Johannes Everse; Kathleen E. Everse, both of 2613 Newcomb St., Lubbock, Tex. 79430; Leo C. Mercer, 4800 Alberta, El Paso, Tex. 79912

[21] Appl. No.: 74,983

[22] Filed: Sep. 13, 1979

[51] Int. Cl.$^3$ .................. A61L 15/03; A61F 13/00; A61K 9/70

[52] U.S. Cl. ........................... 424/14; 424/16; 424/19; 424/28; 424/94; 128/260

[58] Field of Search .................. 435/174–182; 424/94, 14, 16, 19–22, 27, 28, 78–83; 128/260

[56] References Cited

U.S. PATENT DOCUMENTS

| | | | |
|---|---|---|---|
| 3,522,346 | 7/1970 | Chang | 424/94 |
| 3,639,213 | 2/1972 | Ginger et al. | 424/94 |
| 3,715,277 | 2/1973 | Dinelli et al. | 435/182 |
| 3,730,841 | 5/1973 | Salvatore et al. | 435/182 |
| 3,809,605 | 5/1974 | Schmitt et al. | 435/182 |
| 3,826,678 | 7/1974 | Hoffman et al. | 424/36 |
| 3,865,726 | 2/1975 | Chibata et al. | 424/94 |
| 3,875,008 | 4/1975 | Yashino et al. | 435/182 |
| 3,980,772 | 9/1976 | Ginger et al. | 424/94 |
| 3,985,616 | 10/1976 | Weaver et al. | 435/182 |
| 4,004,979 | 1/1977 | Avrameas et al. | 424/94 |
| 4,004,980 | 1/1977 | Emery et al. | 435/182 |
| 4,029,767 | 6/1977 | Valrez et al. | 424/94 |
| 4,061,141 | 12/1977 | Hyden et al. | 435/182 |
| 4,169,014 | 9/1979 | Goldberg | 435/182 |
| 4,178,368 | 12/1979 | Heimberger et al. | 424/94 |

*Primary Examiner*—Shep K. Rose

[57] ABSTRACT

The invention comprises the construction of an implantable device consisting of a clot lysing inhibitor immobilized onto a biocompatible polymer, and the method of regulation of blood clotting time, the prevention of blood clot formation, and the hydrolysis of existing blood clots with the use of said device. A method is also disclosed to prevent the growth of fibrous connective tissue on prosthetic devices.

9 Claims, 2 Drawing Figures

IMMOBILIZATION OF STREPTOKINASE

STATE OF THE ART

Streptokinase is an FDA approved drug that has been used in the treatment of thrombosis, pulmonary embolisms, and other clotting-induced maladies. The enzyme was originally discovered by Tillett in 1933 in hemolytic streptococci and was subsequently known to be an activator of human plasminogen. The enzyme is capable of promoting the lysis of experimentally induced thrombi as well as of spontaneously occurring venous and arterial thrombi.

During the 1960's a vast amount of literature accumulated on the clinical use of streptokinase, which culminated in an extensive trial on its usefulness as a fibrinolytic agent, the Urokinase-Streptokinase Embolism Trial of (1974) J.A.M.A. 229: 1606. This trial studied 167 patients, and it was concluded that streptokinase as well as urokinase may be safely used in humans and that these enzymes provide a beneficial alternative to heparin, W. R. Bell (1977) Urokinase in the treatment of Pulmonary Emboli. In: Thrombosis and Urokinase, R. Paoletti and S. Sherry, Eds., Academic Press, New York, p. 153.

Several factors, however, contributed to the decline in the use of streptokinase. Most of all, repeated injections of streptokinase rapidly leads to an immune response. Streptokinase is a potent antigen and problems relating to its antigenicity caused a major shift from interest in streptokinase to urokinase. The problem of antigenicity is augmented by the fact that streptokinase has a relatively short half-life in vivo and frequent injections are necessary in order to promote a continuous fibrinolytic action. (In the Urokinase-Streptokinase Embolism Trial 100.000 units per hour were administered for a period of 24 hours). The circulating half-life of streptokinase is about 30 hrs.

The major problem that is encountered with the use of urokinase or streptokinase is an increased tendency for bleeding, especially when high levels of the enzymes are used. This effect considerably limits the usefulness of the enzymes, especially in the post-surgical state where the need for an effective thrombolytic agent may be quite great.

There are indications that streptokinase would be preferable to urokinase as a thrombolytic agent, were it not for its antigenic effects. The advantages may be summarized as follows:

(a) Streptokinase may readily be obtained in large quantities whereas the source of urokinase is limited. This is clearly reflected in the price of the enzymes.

(b) The circulating half-life of streptokinase is much longer than that of urokinase; smaller amounts are therefore required to achieve the same thrombolytic agents.

The development of urokinase as a thrombolytic agent resulted mainly from a search for a thrombolytic agent that did not induce an immune response. Although the enzyme has an extremely short circulating half-life (8-10 min.) it has found wide application in the treatment of embolisms. The greatest benefit was found in patients with acute emboli (less than 10 days old) whereas only marginal benefits were observed in patients with subacute or chronic emboli. Urokinase as well as streptokinase have successfully been used in the treatment of myocardial infarctions, cerebral infarctions, deep vein thrombosis and pulmonary emboli.

Immobilized streptokinase has been prepared by Rimon et al (Rimon, A., Gutman, M., and Rimon, S. Studies on the activation of plasminogen. Preparation and properties of an insoluble derivative of streptokinase. Biochem. Biophy. Acta 73, 301, 1963.) using a diazotized copolymer of p-aminophenylalanine and leucine. These authors utilized the immobilized streptokinase to study the mechanism of activation of plasminogen. No data were presented concerning the stability of the immobilized enzyme. Recently Sugitachi et al (Sugitachi, A., Takagi, K., Imaoka, S., and Kosaki, G. Immobilization of plasminogen activator, urokinase, on nylon. Thrombos. Haemostas (Stuttg.) 39, 426, 1978.) reported the immobilization of urokinase on nylon. The authors demonstrated a greatly increased stability of the urokinase as a result of the immobilization. Preparations were stable at 4° C. for up to 6 months and heating of the nylon-bound urokinase to 70° C. for 10 min. only slightly affected the fibrinolytic activity, whereas soluble urokinase was completely inactivated under these conditions.

STATEMENT OF THE INVENTION

The invention comprises the construction of an implantable device consisting of a clot lysing initiator immobilized onto a biocompatible polymer, and the method of controlling blood clotting (i.e., the regulation of blood clotting time, the prevention of blood clot formation, and the hydrolysis of existing blood clots) with the use of said device.

Furthermore, a method is disclosed to prevent the growth of fibrous connective tissue on prosthetic devices.

The clot-lysing initiators can be immobilized on nylon, dacron, collagen, polyvinylpyrolidone, copolymeric p-aminophenylalanine and leucine, or any other material approved for use inside living humans.

GENERAL DESCRIPTION OF THE DRAWINGS

FIG. 1 is a graph showing blood clotting time in rabbits as a function of streptokinase administration. Soluble streptokinase (200 I.U./kg) was injected intravenously into a rabbit at the times indicated by arrows. Immobilized streptokinase (200 I.U./kg) was implanted subcutaneously into another rabbit and removed 150 days later. A third (control) rabbit received a sham implant.

Figure 2:
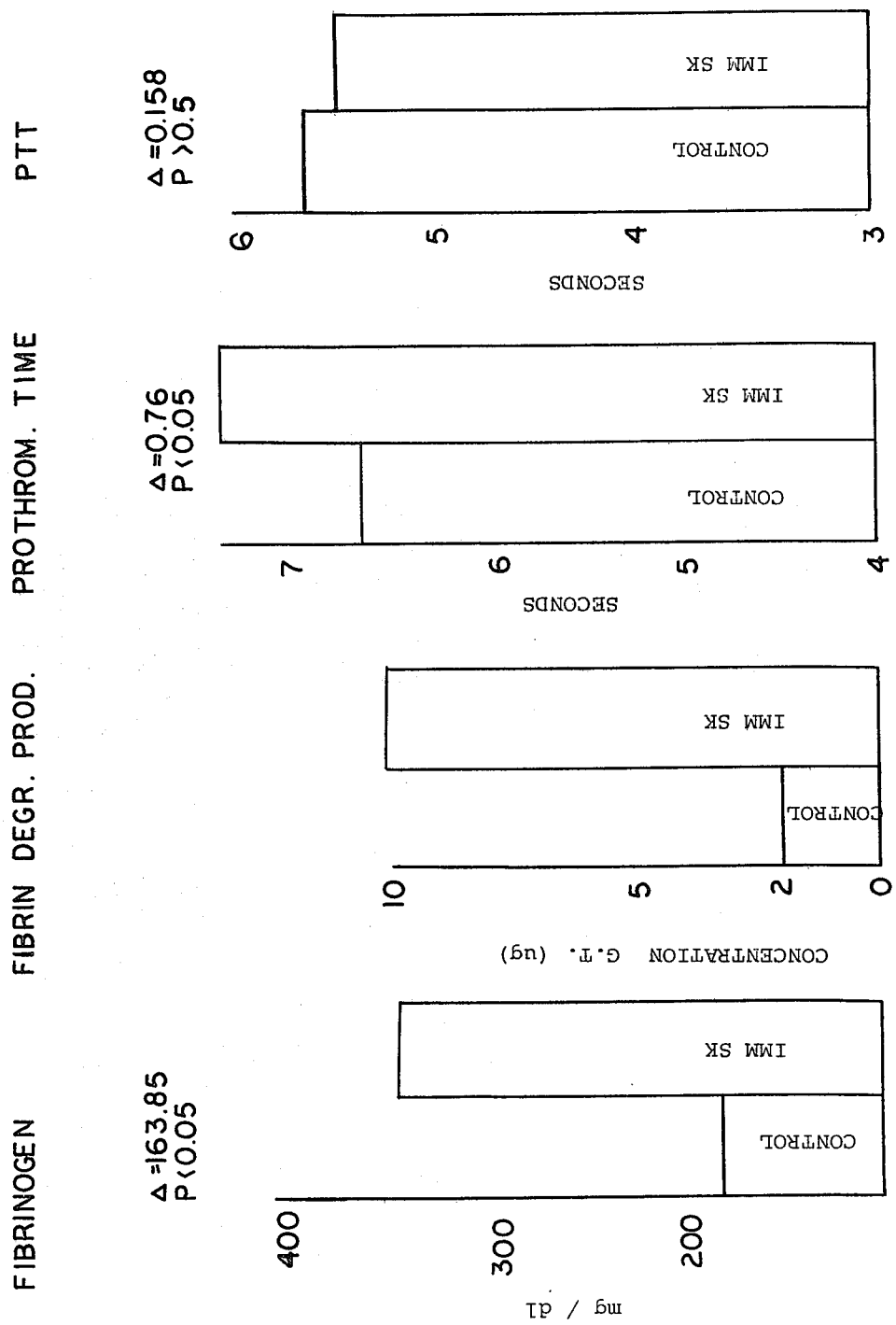

FIG. 2 is a view showing the changes in blood constituents during implantation of immobilized streptokinase. The concentration of serum fibrin degradation products increased about five-fold, whereas the concentration of fibrinogen increased about three-fold. Relatively small and possibly insignificant changes were found in the prothrombin time and the partial thromboplastin time. No significant changes were found in the platelet counts and the euglobulin lysis time.

PREFERRED EMBODIMENT

Streptokinase (Varidase) was purchased from Lederle Laboratories, Inc. and used without further purification. Nylon-66 was used as single fibers as well as woven into cloth. All other chemicals were of reagent grade.

(a) Partial Hydrolysis

Nylon 66 is partially hydrolyzed by heating the nylon for 1 hour at 50° C. in sufficient 4 N HCl to completely cover the nylon. After the partial hydrolysis the nylon is thoroughly washed with water to remove all acid and is subsequently dried in air overnight. The nylon is finally put in an oven at 90° C. for 1 and ½ hours to ensure complete dryness.

(b) Preparation of PNB-nylon

The dry nylon is put into a round bottom flask and covered with a solution of 10% by volume triethanolamine in chloroform. Fifty mg. of p-nitrobenzoylchloride per gram of nylon is then added and the mixture is refluxed for at least 12 hrs. At the end of this period the PNB-nylon is thoroughly washed with dry chloroform and dried in air.

(c) Reduction

The PNB-nylon is put into a round bottom flask and covered with a solution of 10% dithionite in water. The mixture is refluxed for 1 hr. The nylon is then thoroughly rinsed with acidified water until no more dithionite is detectable.

(d) Diazotization and Coupling

The wet PNB-nylon is transferred to a beaker which is placed in ice. The nylon is covered with 200 ml 1 N HCl+20 ml 2 N sodium nitrite, and the mixture is kept in ice for 1 hr. The nylon is then thoroughly washed with ice-cold water and the diazotized nylon is spread out in a flat dish that is placed in ice. Five ml of sterile water containing 20.000 I.U. of streptokinase are added to the nylon and the coupling is allowed to proceed for 1 hr. in ice. All of the nylon should be kept in constant contact with the streptokinase solution during the period in order to ensure uniform coupling.

After the coupling is completed the streptokinase-nylon is thoroughly washed with sterile water until soluble streptokinase has been removed. The streptokinase-nylon may be stored moist at 0° C. to 5° C.

The implantation of the nylon into rabbits was done after providing a local anesthesia with Novacaine. The nylon was soaked for 15 min. in a penicillin solution prior to the implantation. The closing of the wound generally required about 6 stitches.

Nylon fibers containing 2000 I.U. streptokinase per kg body weight, were implanted subcutaneously into a rabbit. A control rabbit received an equal amount of nylon fibers which did not contain any streptokinase. Since the thrombolytic activity is only indirectly provided by the streptokinase it was not necessary for the streptokinase to be present in the bloodstream itself. Plasminogen is present in the interstitial fluids and the plasmin is able to diffuse freely into and out of the circulatory system. The presence of streptokinase in the interstitial fluids was sufficient to obtain the desired effects. Furthermore, the restriction of the streptokinase to the interstitial fluids was advantageous in further reducing the rate of antibody formation by the enzyme.

The results are shown in FIG. 1. Blood clotting time was measured by drawing a drop of blood from the marginal ear vein into a Clay-Adams capillary tube and breaking a piece of the tube every 10 sec. until fibrin strands appeared. The blood clotting time, which was close to 1 min, before the implantation of the immobilized streptokinase, increased to about 3.5 min. within 2 days after the enzyme was implanted and subsequently decreased to about 3 min. It then remained stable at this value for 150 days. During this time the rabbit appeared healthy and comfortable in all respects.

No difficulties were encountered with the wound that was created by the implantation. No excessive bleeding occurred during surgery and the wound healed nicely, although somewhat slower than one would have expected. In due time the hair grew back and the implanted nylon was only noticeable by feeling. The rabbit did not seem to be more sensitive than normal around the area of implantation.

After 150 days following the implantation we could not detect any antibody formation against the immobilized streptokinase in the rabbit's serum, using the Ouchterlony technique. The fact that the immobilized streptokinase remained fully active during the 150-day period shows that little if any antigenic response was elicited by the immobilized enzyme.

After 150 days the implanted nylon-bound streptokinase was surgically removed. We observed that a richly vascularized membrane had formed around the implanted nylon. No connective tissue growth had occurred through the nylon fiber plug, and all implanted nylon could readily be removed. As shown in FIG. 1, the blood clotting time returned to normal within a few days following removal of the streptokinase.

Some data concerning changes in several blood factors that occurred as a result of the implantation of the immobilized streptokinase are shown in FIG. 2. The concentration of serum fibrin degradation products increased about five-fold, whereas the concentration of fibrinogen increased about three-fold. Relatively small and possibly insignificant changes were found in the prothrombin time and the partial thromboplastin time. No significant changes were found in the platelet counts and the euglobulin lysis time.

FIG. 1 indicates that immobilization of streptokinase greatly increases its stability in vivo. Immobilized streptokinase appears to exert its action for at least half a year without any apparent loss in activity. Such a stability represents a tremendous increase over the circulatory half-life of soluble streptokinase, which is about 30 hours, and suggests that immobilized streptokinase may be useful in cases where prolonged therapy is required.

These results indicate that the changes in these blood constituents are similar to those observed with soluble streptokinase or urokinase and no adverse reactions resulting from the use of immobilized enzyme are indicated by these data.

As pointed out earlier the use of streptokinase for therapeutic purposes has greatly declined because of its antigenic properties. We were unable to detect any antibodies against soluble streptokinase in the rabbit serum using the Ouchterlony diffusion technique. The Ouchterlony technique is not very sensitive and small amounts of antibodies may not be detectable by this method. It should be noted, however, that no appreciable decrease in the streptokinase activity was observed during the time it was implanted, which strongly supports the hypothesis that no antibodies were formed that could inhibit the enzyme.

The observed increase in fibrin degradation products in the rabbit serum is expected and appears to be similar to the increase found when soluble streptokinase or urokinase are used.

The increase in fibrinogen levels may be due to an increase in the synthesis of fibrinogen, but further experiments are necessary to explain this phenomenon.

The finding that nylon-streptokinase somehow prevents the growth of fibrous tissue around it is a very important observation and detailed experiments are presently in progress to investigate this phenomenon. The absence of this material assures a continuous contact between the nylon-bound streptokinase and the interstitial fluid, and a rapid distribution of the plasminogen and plasmin is further aided by the presence of the vascularized membrane. A similar lack of fibrous growth and the formation of a vascularized membrane occurs when streptokinase is co-immobilized with other enzymes on nylon implants.

Blood clotting time is directly proportional to the amount of immobilized clot-lysing initiator in contact with body fluid. The duration of blood clotting control is determined by the length of time the body fluid is in contact with immobilized clot-lysing initiators. Streptokinase and urokinase are useful as immobilized clot-lysing initiators.

The results presented here suggest that immobilized streptokinase could successfully be used in the treatment of thromboembolic diseases that require prolonged fibrinolytic therapy. In addition, immobilized streptokinase could be valuable in preventative therapy in cases of anticipated thromboembolic problems.

The embodiments of the invention in which an exclusive property or privilege is claimed are defined as follows:

1. The process of control of blood clotting in a living mammal comprising:
   providing a clot-lysing initiator immobilized on a solid water insoluble non-colloidal substrate; and
   implanting said initiator supporting substrate in the body of said living mammal in contact with its body fluid.

2. The process recited in claim 1 wherein said initiator is selected from the group consisting of streptokinase and urokinase.

3. The process recited in claim 1 wherein said carrier substrate has a form selected from the group consisting of tubular material, fiber material and woven cloth.

4. The process recited in claim 1 wherein said carrier substrate is selected from the group consisting of nylon, copolymeric p-aminophenylalanine and leucine, dacron, collagen and polyvinylpyrolidone.

5. The process recited in claim 1 wherein said carrier substrate is subcutaneously implanted in an animal.

6. The process recited in claim 4 wherein said animal is a human and said body fluid is selected from the group consisting of blood and interstitial fluid.

7. A blood clotting control device comprising: a body fluid contacting means comprising, a solid water insoluble non-colloidal carrier substrate and immobilized clot lysing initiator carried by said solid carrier substrate, said solid carrier substrate and clot lysing initiator being adapted to be implanted in a living mammal in contact with the body fluids thereof.

8. The device recited in claim 7 wherein said immobilized clot-lysing initiator is selected from the group consisting of streptokinase and urokinase.

9. The device recited in claim 7 wherein said substrate consisting of a material selected from the group consisting of nylon, copolymeric p-aminophenylalanine and leucine, dacron, collagen and polyvinylpyrolidone; and said substrate further consisting of a form selected from the group comprising fiber, tube and woven cloth.

* * * * *